United States Patent [19]

Lane et al.

[11] 3,978,140

[45] Aug. 31, 1976

[54] PROCESS FOR THE PREPARATION OF CARBINOLS

[75] Inventors: Clinton Fisher Lane, Franklin; Hal Leslie Myatt, Milwaukee, both of Wis.

[73] Assignee: Aldrich-Boranes, Inc., Milwaukee, Wis.

[22] Filed: Sept. 23, 1974

[21] Appl. No.: 508,281

[52] U.S. Cl. .................. 260/617 C; 260/618 H; 260/611 A; 260/638 A; 260/622 R
[51] Int. Cl.$^2$ .................................. C07C 29/00
[58] Field of Search ........ 260/617 C, 618 H, 638 A, 260/618

[56] References Cited
UNITED STATES PATENTS

| | | | |
|---|---|---|---|
| 2,874,165 | 2/1959 | Brown | 260/618 |
| 2,945,886 | 7/1960 | Brown | 260/570.9 |
| 3,634,277 | 1/1972 | Brown | 260/618 |

OTHER PUBLICATIONS

Brown et al., J.A.C.S., vol. 82, pp. 681–686 (1960).
Brown et al., J.A.C.S., vol. 92, pp. 1637–1644 (1970).
Anhoury et al., J. Chem. Soc., Perkin Trans 1, 191 (1974).

*Primary Examiner*—James O. Thomas, Jr.
*Assistant Examiner*—James H. Reamer
*Attorney, Agent, or Firm*—Merriam, Marshall, Shapiro & Klose

[57] ABSTRACT

Organic compounds containing a carboxylic acid or carboxylic acid anhydride group are reduced when contacted with an alkali metal borohydride and a boron trihalide in a liquid medium in which diborane is soluble in the form of a labile borane adduct. Hydrolysis of the reaction mixture then provides a useful synthesis of the corresponding carbinols.

The alkali metal borohydride-boron trihalide reagent may either be preformed and reacted subsequently with an organic compound containing a carboxylic acid or anhydride group, or the alkali metal borohydride-boron trihalide reagent may be produced in the presence of an organic compound containing a carboxylic acid or anhydride group. This development makes it possible to synthesize a wide variety of carbinols which are valuable and useful intermediates in organic synthesis.

1 Claim, No Drawings

PROCESS FOR THE PREPARATION OF CARBINOLS

BACKGROUND OF THE INVENTION

1. Field of Invention

This invention relates to a novel process for the preparation of carbinols by the reduction of a carboxylic acid or carboxylic acid anhydride group in organic compounds containing one or more such groups. More particularly, this invention provides a process for the preparation of carbinols whereby an organic compound containing a carboxylic acid or carboxylic acid anhydride group, an alkali metal borohydride, and a boron trihalide are contacted in a liquid medium in which diborane is soluble in the form of a labile borane adduct. Hydrolysis of the resulting reaction mixture then yields the corresponding carbinol formed by hydrogenation of the carboxylic acid or carboxylic acid anhydride group.

2. Description of the Prior Art

In U.S. Pat. No. 2,856,428, Herbert C. Brown disclosed that the addition of relatively minor amounts of aluminium chloride to solutions of sodium borohydride in the dimethyl ether of diethylene glycol (diglyme) greatly increases the reducing rates and capacities of the borohydride. This reagent rapidly reduces aldehyde, ketone, ester, carboxylic acid, nitrile, and amide groups. The reagent described by Brown consisted of an alkali metal borohydride and a halide of a polyvalent metal having a valence greater than two and less than six, such as aluminium chloride, gallium chloride, etc., in a liquid carrier such as diglyme. These reagents described by Brown did not include halides of metalloids, such as boron trihalides. The addition of a stoichiometric quantity of a boron trihalide to a solution of an alkali metal borohydride in diglyme results in the rapid evolution of diborane with the expected loss of the active hydride of the solution. Consequently, such a reagent is inoperative for reducing and hydrogenating chemical compounds.

Brown has disclosed in U.S. Pat. No. 2,945,886 that a reagent consisting of a boron trihalide and an alkali metal borohydride is exceedingly effective, under certain specific conditions, in enhancing the reducing properties of alkali metal borohydrides. Conspicuously omitted from this U.S. Pat. No. 2,945,886 was any discussion of the use of this procedure to reduce the carboxylic acid group.

The process claimed in U.S. Pat. No. 2,945,886 comprises reducing a chemical compound having a nitrile group by associating, in a inert liquid carrier, one component of a reagent consisting of an alkali metal borohydride and a boron trihalide with the other component of the reagent in the presence of the compound to be reduced. Thus, a mixture of a boron trihalide and the compound to be reduced, specifically a nitrile containing compound, is added slowly to a solution of the alkali metal borohydride. Alternatively, the boron trihalide is added slowly to a solution of the alkali metal borohydride containing the nitrile substituted compound. Serious disadvantages exist in this process. The recommended solvent, diglyme, is relatively expensive and thus limits the large scale commercial utility of this process. Also, the process is limited to functional groups which react rapidly with the diborane as formed, otherwise the diborane would vaporize away from the reaction mixture and cause serious problems.

The process of reducing a chemical compound having a reducible functional group by adding the compound to a reagent in which an alkali metal borohydride and a boron trihalide are previously combined in a liquid carrier is not described by Brown in U.S. Pat. No. 2,945,886.

The reaction of sodium borohydride dissolved in diglyme with boron trifluoride is known to generate diborane gas, $B_2H_6$, an extremely useful chemical with many remarkable properties (H. C. Brown, *Hydroboration*, W.A. Benjamin, Inc., New York, New York, 1962). Diborane is an exceedingly powerful, but selective hydrogenating agent for functional groups as disclosed by Brown in U.S. Pat. No. 2,874,165 and in his recent book *Boranes in Organic Chemistry*, Cornell University Press, Ithaca, New York, 1972. Brown and Rao in *J. Am. Chem. Soc.*, 82, 681 (1960) disclose diborane preformed by reaction of sodium borohydride and boron trifluoride etherate in diglyme in a separate vessel and passed over as a gas to a reaction vessel for use in reducing carboxylic acids in diglyme or tetrahydrofuran.

Diborane is a highly reactive gas which rapidly decomposes on exposure to air and moisture. Consequently, it is difficult to handle. Fortunately, diborane is highly soluble in tetrahydrofuran where it exists in the form of a labile borane-tetrahydrofuran adduct of the formula:

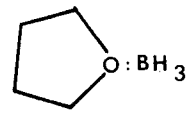

This adduct formation greatly increases the solubility of diborane in tetrahydrofuran and makes it possible to prepare and ship solutions which are up to one molar in borane ($BH_3$). In other common ether solvents, which do not readily form an ether-borane adduct, the solubility of diborane is quite low. Examples include diethyl ether, diisopropyl ether, and diglyme. Borane reductions performed in such solvents are potentially very dangerous because of the possibility of escape of diborane gas from the reduction media.

Brown has disclosed in U.S. Pat. No. 3,634,277 that the borane-tetrahydrofuran solutions can be prepared without handling the gas by treating suspensions of sodium borohydride in tetrahydrofuran with boron trifluoride followed by filtering or centrifuging the tetrahydrofuran solution of the borane-tetrahydrofuran complex from the precipitated sodium tetrafluoroborate. These borane-tetrahydrofuran solutions have been found to be useful for selective hydrogenations and reductions [H. C. Brown, P. Heim, and N. M. Yoon, *J. Am. Chem. Soc.*, 92, 1637 (1970)].

In a copending application Ser. No. 334,642, filed Feb. 22, 1973, now U.S. Pat. No. 3,882,037, the entire contents of which is incorporated herein by reference by permission of the assignee, Herbert C. Brown disclosed that the presence of an aliphatic, alicyclic, or cyclic sulfide greatly stabilizes the borane-tetrahydrofuran reagent permitting the storage of such solutions for long periods of time at ambient temperatures. Such stabilized solutions can be prepared without handling diborane gas by treating a suspension of an ionic borohydride in tetrahydrofuran, containing an aliphatic, alicyclic, or cyclic sulfide, with boron trifluoride, followed by removal at ambient temperatures of the precipitated sodium tetrafluoroborate.

The solutions of labile borane complexes in tetrahydrofuran are the most convenient reagents to use for borane reductions on a laboratory scale. Unfortunately, major difficulties arise when these solutions of labile borane complexes in tetrahydrofuran are applied to large scale commercial reductions of chemical compounds. Since the vapor pressure of diborane above these tetrahydrofuran solutions is relatively high, the solutions are usually manufactured in relatively low concentrations not exceeding one molar in $BH_3$. This means that large amounts of solvent must be handled and transferred for a relatively small quantity of borane. Another disadvantage of such a dilute solution is that the amount of organic compound that can be reduced per unit batch size is severely limited by the dilute concentration of the borane.

The most serious difficulties which limit the use of the tetrahydrofuran solutions of labile borane complexes for lage scale commercial reductions, result from the problems associated wih the processing of the mixtures to remove the solid sodium tetrafluoroborate. Because these borane solutions are extremely air-sensitive, specialized filtration and centrifugation process equipment is required along with specialized handling and transfer techniques. But even with the most careful processing procedures there is always an unavoidable loss of "active hydride" during these manipulations. This loss of active hydride is caused by the volatility of diborane and by the difficulty and virtual impossibility of achieving and maintaining thoroughly dry process equipment, thoroughly dry filters and completely airtight systems. Another problem is the incompatibility of labile borane complexes with many commercial filters. For example, cellulose-derived filters cannot be used because of the presence of active hydrogens in this material. Also tetrahydrofuran is an excellent solvent for polymeric materials. Therefore, the choice of filter material is further limited. But an even more serious limitation which results from the superior solvent properties of tetrahydrofuran is that no known elastomers will withstand prolonged contact with tetrahydrofuran. Consequently, none of the gaskets in the filtration or centrifugation equipment can be made from the common, normally utilized Viton, buta-N, neoprene, or natural rubber elastomers. Economically, the processing required to remove the solid sodium tetrafluoroborate is a disadvantage because it is very time consuming and therefore quite expensive. Also, some of the active hydride content of the mixture is always lost in the removed solid material.

All of these disadvantages and difficulties have now been overcome by the use of the present invention.

SUMMARY OF THE INVENTION

The present invention provides a new and novel process for reducing a chemical compound having a carboxylic acid or carboxylic acid anhydride group by contacting in a liquid medium in which diborane is soluble as a labile borane adduct, an alkali metal borohydride, a boron trihalide, and the organic compound to be reduced all advisably present about in the stoichiometrical amounts required for reduction of the carboxylic acid or carboxylic acid anhydride group. The use of this new process eliminates the serious disadvantages and difficulties present in the old process which utilized a clear solution of borane-tetrahydrofuran produced by filtering off the insoluble sodium tetrafluoroborate.

After the compound is reduced, the reaction mixture is hydrolyzed with water, the organic layer is separated and the carbinol is isolated from the organic layer.

A mixture of a boron trihalide and the compound to be reduced may be added slowly to an alkali metal borohydride in a suitable liquid medium. Alternatively, the boron trihalide can be added to a mixture of the compound to be reduced and an alkali metal borohydride in a suitable liquid medium. Also, the compound to be reduced, a boron trihalide, and an alkali metal borohydride can all be added simultaneously to a suitable liquid medium. Preferably, however, the compound to be reduced is added slowly to a reagent mixture prepared from an alkali metal borohydride and a boron trihalide in a liquid medium in which diborane is soluble as a labile borane adduct. Regardless of which procedure is used, the chemical compound is reduced in the liquid medium in the presence of any by-product which is formed.

The reduction process is generally carried out at a temperature of from about −30°C to +70°C. A higher temperature may be used but the temperature should be sufficiently low so that the boron hydrides do not substantially thermally decompose.

The new process can be carried out at a low temperature where the solubility of diborane is increased without any need to allow the solution to reach room temperature. In this way the concentration of borone can be increased substantially. Reagent mixtures with a contained $BH_3$ concentration as high as four molar can be prepared and utilized directly for the reduction process thus increasing the amount of compound that can be reduced per unit batch size. Also, the amount of solvent required is, of course, decreased giving additional economic savings.

Depending on the specific alkali metal borohydride and boron trihalide used for the reduction, there is obtained as a by-product either an alkali metal tetrahaloborate or an alkali metal halide. Furthermore, the alkali metal tetrahaloborate or alkali metal halide may be soluble or insoluble in the particular liquid reaction medium used for the reduction. The solubility of the inorganic by-product is dependent upon the following: the liquid medium, the alkali metal borohydride, and the boron trihalide. For example, sodium borohydride plus boron trifluoride in tetrahydrofuran gives insoluble sodium tetrafluoroborate; sodium borohydride and boron trifluoride in diglyme containing dimethyl sulfide solubilizes the resulting sodium tetrafluoroborate; sodium borohydride plus boron trichloride in either tetrahydrofuran or diglyme containing dimethyl sulfide gives insoluble sodium chloride; and lithium borohydride plus boron trifluoride in either tetrahydrofuran, diglyme or diethyl ether containing dimethyl sulfide gives soluble lithium tetrafluoroborate. Nevertheless, it is a feature of the invention to effect the reduction of the compound containing the carboxylic acid or carboxylic acid anhydride group in the reaction mixture without separating either the alkali metal tetrahaloborate or alkali metal halide. The most important improvement is the complete elimination of the costly, time-consuming, and technically difficult removal of the alkali metal tetrahaloborate or alkali metal halide. In this new process the reduction of the organic compound has been found to proceed quite adequately in the presence of the inorganic by-product, i.e., alkali metal tetrahaloborate or alkali metal halide. When the reduction is complete, the reduced organic compound is isolated by simple hydrolysis of the reaction mixture. The inorganic by-products dissolve in the aqueous layer and the carbinol is isolated by extraction into an organic solvent or by filtration.

By utilizing as the liquid medium a solvent for diborane which forms a labile borane adduct, the present invention is a definite improvement over the older process which specified as the liquid carrier a solvent for the alkali metal borohydride. (U.S. Pat. No. 2,945,886). In the old process it was not possible to combine the alkali metal borohydride and a boron trihalide prior to the introduction of the compound to be reduced because the active reducing agent, diborane, would have vaporized away from the reagent in a liquid carrier in which the diborane was not soluble. With the present improvement, the alkali metal borohydride and the boron trihalide can be combined prior to the addition of the compound to be reduced to give a more selective reducing reagent mixture, i.e., a mixture of a labile borane adduct and an inert inorganic by-product, i.e., an alkali metal tetrahaloborate or alkali metal halide. Thus, this reagent can be used to cleanly reduce organic compounds that are normally sensitive to either the strongly basic alkali metal borohydride or the strongly acidic boron trihalide.

Even in the case where the reagent is generated in the presence of the compound to be reduced, the present invention, which utilizes as the liquid medium a solvent in which diborane is soluble as a labile borane adduct, is an improvement over the old process, which utilized as the liquid carrier a solvent for the alkali metal borohydride (U.S. Pat. No. 2,945,886). The scope of the old process was limited to the functional groups which react rapidly with the diborane as formed because otherwise the diborane would be lost from the reaction mixture. Also, the preferred solvent for the old process was diglyme which is relatively expensive and available commercially only in a relatively impure grade that requires extensive purification prior to use and which frequently causes problems during subsequent work-up because diglyme is completely miscible with both water and most common organic solvents. The present invention using tetrahydrofuran as the preferred solvent has eliminated these disadvantages.

An organic liquid medium in which diborane is soluble as a labile borane adduct is necessary for the successful performance of the present invention. Although other solvents may satisfy this requirement, the preferred liquid media are tetrahydrofuran, in which diborane dissolves to form a reactive borane-tetrahydrofuran adduct, and an inert liquid medium containing an organic sulfide in which diborane readily dissolves to form a reactive labile borane-organic sulfide complex. On the other hand, any amine which forms a highly stable borane adduct and thus deactivates the borane for reductions is not recommended.

The capacity of an inert solvent such as diethylether, monoglyme, diglyme and triglyme, as well as tetrahydrofuran, to dissolve diborane and the stability of the resulting reagent mixture is greatly improved by having an organic aliphatic, alicyclic, or cyclic sulfide present in the inert solvent. Aliphatic sulfides, such as dimethyl sulfide, methylethyl sulfide, diethyl sulfide, methylpropyl sulfide, methylbutyl sulfide, and other lower alkyl sulfides; alicyclic sulfides, such as methylcyclopentyl sulfide and methylcyclohexyl sulfide; cyclic sulfides, such as tetramethylene sulfide, pentamethylene sulfide and heptamethylene sulfide; and disulfides, such as 1,3-dithiomethylpropane, $CH_3SCH_2CH_2CH_2SCH_3$ can be used. The sulfides can contain inert substituents, such as methoxy and methyl groups, as in $CH_3OCH_2CH_2SCH_3$ and 2-methyltetramethylene sulfide. For greatest effectiveness, it is desirable that the molecular weight of the sulfide be low, preferably below 200, so that relatively high molar concentrations can be achieved in the liquid reaction medium. It is preferred that the concentration of the sulfide used to stabilize diborane solutions be equal, on a molar basis, to the concentration of borane ($BH_3$) in the solution.

The boron trihalides preferred for use in the process are boron trifluoride and boron trichloride although boron tribromide and boron triiodide can also be used.

The preferred reagent of the present invention consists of sodium borohydride and either boron trifluoride (four moles per three moles of sodium borohydride) or boron trichloride (one mole per three moles of sodium borohydride) in either tetrahydrofuran or tetrahydrofuran containing dimethyl sulfide (four moles per three moles of sodium borohydride). The boron trihalide can be added as a gas or in the form of its addition compound with an ether, such as diethyl ether, tetrahydrofuran, anisole, etc. However, boron trifluoride diethyl etherate is the preferred reactant.

The term "alkali metal borohydride" as used herein is intended to mean the simple alkali metal borohydrides, such as lithium borohydride, sodium borohydride, and potassium borohydride. Potassium borohydride can be used but has a lower solubility in organic solvents than sodium borohydride. Lithium borohydride is readily soluble in a large variety of solvents, but its cost at present is much greater than sodium borohydride. Consequently, the preferred reagent at the present time is sodium borohydride.

The scope and utility of this novel new process for the preparation of carbinols is indicated by the wide variety of carboxylic acids that can be reduced cleanly in excellent yields. For example, aliphatic acids, alicyclic acids, heterocyclic acids, aromatic acids, dicarboxylic acids, carboxylic acid anhydrides, and organic compounds containing one or more carboxylic acid groups in addition to one or more other potentially reactive substituents [such as a fluoro, chloro, bromo, iodo, hydroxy, alkoxy, aryloxy, benzyloxy, amino, alkylamino, arylamino, benzylamino, amido, N-alkylamido, N-arylamido, N-benzylamido, nitro, nitroso, hydrazine, N-arylhydrazine, N-benzylhydrazine, oxime, sulfide, disulfide, sulfonyl, alkylsulfonyl, arylsulfonyl, benzylsulfonyl, halosulfonyl, sulfonic acid, sulfinic acid, sulfamido, ester, acid chloride, keto, aldehyde, epoxide, ketal, or acetal group] can all be reduced readily and highly selectively to he corresponding carbinol or functionally substituted carbinol using the process of the present invention. The only organic functional groups which will not tolerate the conditions required to carry out the present process are strong oxidizing groups such as peroxides and peracids and carbon-carbon unsaturations, which undergo competitive hydroboration.

DESCRIPTION OF THE PREFERRED EMBODIMENTS

This invention can be further understood by reference to the following examples.

EXAMPLE 1

A 22-liter, 4-necked glass reaction vessel equipped with a mechanical stirrer, thermometer, pressure-equalizing addition funnel and reflux condenser vented to a mercury bubbler was charged with 567 grams (14.25 moles plus 5% excess) of sodium borohydride, and flushed for 0.5 hour with dry nitrogen. Tetrahydrofuran (7.5 liters) was then added and the resulting slurry was cooled to 5°C with stirring using an external dry ice/isopropyl alcohol bath. The addition funnel was charged with 2.33 liters (19 moles) of boron trifluoride diethyl etherate which was then added dropwise to the reaction mixture with stirring over a 2 hour period while maintaining a reaction temperature of 0°–5°C.

After stirring the reaction mixture for an additional 0.5 hour at 0°–5°C, a solution of 3860 grams (18 moles) of m-phenoxybenzoic acid in tetrahydrofuran was added dropwise over a 4 hour period while maintaining a reaction temperature of 0°–10°C. When the addition was complete, the reaction mixture was stirred for 12 hours at 20°C followed by 2 hours at 40°C. The reaction mixture was then transferred to a 10 gallon bottle containing 6 liters of water and 8 liters of diethyl ether. After mixing thoroughly, the aqueous layer was removed and the organic layer was extracted with water (1 × 4 liters), extracted with aqueous saturated sodium bicarbonate solution (1 × 4 liters), extracted with aqueous saturated sodium chloride solution (1 × 4 liters), dried over anhydrous potassium carbonate, filtered, and concentrated on a rotary evaporator. Short-path distillation gave 3000 grams (83% yield) of m-phenoxybenzyl alcohol, bp 135°–140°C/0.10 mm, $n_{20}D$ 1.5935.

EXAMPLE 2

A 500-milliliter, 4-necked glass reaction vessel equipped with a magnetic stirring bar, pressure-equalizing addition funnel, thermometer, and reflux condenser vented to a mercury bubbler was charged with 9.6 grams (0.248 mole plus 5% excess) of sodium borohydride and 64 grams (0.30 mole) of m-phenoxybenzoic acid and flushed 10 minutes with dry nitrogen. The reaction vessel was cooled in an external ice/water bath as 0.2 liter of tetrahydrofuran was added dropwise followed by 40.6 milliliters (0.33 mole) of boron trifluoride diethyl etherate over a 1 hour period while maintaining a temperature of 0°–10°C. The reaction mixture was then stirred for 12 hours at 20°C followed by 2 hours at 40°C. The product was isolated using a procedure similar to that described in Example 1 giving 48 grams (80% yield) of m-phenoxybenzyl alcohol, $n_{20}D$ 1.5935.

EXAMPLE 3

A 3-liter, 4-necked glass reaction vessel equipped as described in Example 1 was charged with 500 grams (1.89 moles) of 11-bromoundecanoic acid and 59.6 grams (1.50 moles plus 5% excess) of sodium borohydride and treated with one liter of tetrahydrofuran, then with 0.246 liter (2.0 moles) of boron trifluoride diethyl etherate while maintaining a temperature of 0°–10°C using essentially the same procedure as described in Example 2. When the addition was complete, the reaction mixture was stirred for one hour at 0°–10°C followed by 2 hours at 25°C. The product was isolated as described in Example 1 giving, after concentration on a rotary evaporator, 442 grams (93% yield) of white, crystalline 11-bromoundecanol, mp 44°–46°C.

EXAMPLE 4

A 22-liter, 4-necked glass reaction vessel equipped as described in Example 1 was charged with 624 grams (15.8 moles plus 5% excess) of sodium borohydride and 3620 grams (20 moles) of o-nitrophenylacetic acid and flushed for 0.5 hour with dry nitrogen. The reaction vessel was cooled to 0°C using an external dry ice/isopropyl alcohol bath as 10 liters of tetrahydrofuran was added dropwise over a 2 hour period. Boron trifluoride diethyl etherate (2.58 liters, 21 moles) was then added dropwise over a 4 hour period while maintaining a reaction temperature of 0°–10°C. The reaction mixture was then stirred for 12 hours at 20°–25°C. Isolation of the product as described in Example 1 gave 2450 grams (73% yield) of o-nitrophenethyl alcohol as a clear, light-orange liquid, bp 112°C/0.15 mm, $n_{20}D$ 1.5644.

EXAMPLE 5

A 2-liter, 4-necked glass reaction vessel equipped as described in Example 1 was charged with 44.6 grams (1.12 moles plus 5% excess) of sodium borohydride, 0.75 liter of tetrahydrofuran, and 0.185 liter (1.5 moles) of boron trifluoride diethyl etherate at 0°–5°C using the procedure described in Example 1. In a separate 3-liter, 4-necked glass reaction vessel equipped as described in Example 1 was placed 148 grams (1.0 mole) of phthalic anhydride and 0.25 liter of tetrahydrofuran. The resulting slurry was cooled to 0°–5°C using an external ice/water bath. The sodium borohydride-boron trifluoride reaction mixture was then transferred under nitrogen pressure to the anhydride/tetrahydrofuran slurry over a 1.5 hour period while maintaining a temperature of 5°–10°C. After stirring the reaction mixture for 12 hours at 20°C, 0.25 liter of water was added dropwise over a one hour period followed by one liter of diethyl ether. The aqueous layer was saturated with anhydrous potassium carbonate and the organic layer was removed. The aqueous layer was extracted with diethyl ether (2 × 0.25 liter) and the combined organic extracts were dried over anhydrous potassium carbonate, filtered, and concentrated on a rotary evaporator giving 131 grams (95% yield) of 1,2-benzene dimethanol as a crystalline solid, mp 58°–60°C.

EXAMPLE 6

A 5-liter, 3-necked glass reaction vessel equipped as described in Example 1 was charged with 62.4 grams (1.65 moles) of sodium borohydride, 1 liter of tetrahydrofuran, and 0.26 liter (2.1 moles) of boron trifluoride diethyl etherate at 0°–5°C using essentially the same procedure as described in Example 1. After stirring the reaction mixture for an additional 15 minutes, a solution of 400 grams (2 moles) of 2-bromobenzoic acid in 1 liter of tetrahydrofuran was added dropwise over a 1.5 hour period while maintaining a temperature of 0°–10°C. When the addition was complete, the reaction mixture was stirred for 6 hours at room temperature. Hydrolysis of the reaction mixture and recrystallization of the product from hexane gave 293 grams (78.5% yield) of 2-bromobenzyl alcohol as light-orange crystals, mp 78°–80°C.

EXAMPLE 7

A 12-liter, 4-necked glass reaction vessel equipped as described in Example 1 was charged with 180 grams (4.75 moles) of sodium borohydride, 4 liters of tetrahydrofuran, 0.485 liter (6.6 moles) of dimethyl sulfide, and 0.74 liter (6.0 moles) of boron trifluoride diethyl etherate at 0°–5°C using essentially the same procedure as described in Example 1. After stirring for a additional 0.5 hour at 20°–25°C, 780 grams (5.5 moles) of 3-cyclopentylpropionic acid was added dropwise over a 3 hour period while maintaining a temperature of 35°–40°C. After standing overnight at room temperature, hydrolysis of the reaction mixture followed by distillation of the crude product gave 613 grams (87.5% yield) of 3-cyclopentyl-1-propanol, bp 93°–95°C at 8 mm, $n_{20}D$ 1.4595.

The foregoing detailed description has been given for clearness of understanding only, and no unnecessary limitations should be understood therefrom, as modifications will be obvious to those skilled in the art.

What is claimed is:

1. A process for the preparation of a carbinol whereby an aliphatic, alicyclic or aromatic carboxylic acid or carboxylic acid anhydride, an alkali metal borohydride and a boron trihalide are brought together simultaneously or sequentially, in tetrahydrofuran containing dimethyl sulfide in which diborane is soluble as a labile borane adduct and with all components present about in the stoichiometrical amounts required for reduction of the carboxylic acid or carboxylic acid anhydride group to an alcohol group and having present during the reduction the alkali metal tetrahaloborate or alkali metal halide formed by reaction of the alkali metal borohydride with the boron trihalide, and hydrolyzing the resulting reaction mixture to produce the carbinol.

* * * * *